US012611174B2

(12) United States Patent
Dhatt et al.

(10) Patent No.: US 12,611,174 B2
(45) Date of Patent: Apr. 28, 2026

(54) COMBINATION OCULAR ULTRASOUND AND OPHTHALMOSCOPE

(71) Applicant: FUJIFILM SonoSite, Inc., Bothell, WA (US)

(72) Inventors: Davin Dhatt, Woodinville, WA (US); Saeed Aliakbari, Snohomish, WA (US); Craig Chamberlain, Seattle, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 153 days.

(21) Appl. No.: 18/517,413

(22) Filed: Nov. 22, 2023

(65) Prior Publication Data

US 2025/0160790 A1     May 22, 2025

(51) Int. Cl.
*A61B 8/00*          (2006.01)
*A61B 8/10*          (2006.01)
(Continued)

(52) U.S. Cl.
CPC .............. *A61B 8/4416* (2013.01); *A61B 8/10* (2013.01); *A61B 8/4227* (2013.01); *A61B 8/4254* (2013.01); *A61B 8/4472* (2013.01); *A61B 8/4477* (2013.01); *A61B 8/463* (2013.01); *A61B 8/5261* (2013.01); *G16H 50/20* (2018.01); *G16H 50/30* (2018.01)

(58) Field of Classification Search
CPC ....... A61B 8/4416; A61B 8/10; A61B 5/7624; A61B 5/7267; G06L 2207/22081; G06L 2207/22084; G01N 29/4481
See application file for complete search history.

(56) References Cited

U.S. PATENT DOCUMENTS 10,342,473 B1 *   7/2019   Berme ................. A61B 5/1036
11,435,460 B2    9/2022   Dhatt
(Continued)

FOREIGN PATENT DOCUMENTS

JP          2021168752 A   * 10/2021

OTHER PUBLICATIONS

JP-2021168752-A (Year: 2021).*
(Continued)

*Primary Examiner* — Nyrobi Celestine
(74) *Attorney, Agent, or Firm* — Colby Nipper PLLC

(57)          ABSTRACT

Systems and methods for a combination ocular ultrasound and ophthalmoscope are described. In some implementations, a combination ocular ultrasound and ophthalmoscope device generates first ultrasound data from an ultrasound scan of an eye of a user using a first ultrasound scanner and generates optical data from an optical scan of the eye of the user using an optical sensor. The device generates an ultrasound image from the first ultrasound data and an optical image from the optical data. A hybrid image can be generated by the device from the first ultrasound data and the optical data, the hybrid image generated through the use of a machine-learned model. The combination ocular ultrasound and ophthalmoscope device can increase diagnosis confidence, injury identification, and patient comfort and experience in comparison to conventional, disconnected ultrasound and ophthalmoscope devices and systems.

20 Claims, 14 Drawing Sheets

1100

Receive first optical data based on light incident or reflected from an eye of a subject
1102

Receive first ultrasound data based on reflections of ultrasound signals transmitted at the eye
1104

Generate combined ocular data, the combined ocular data comprising a prediction output by a machine-learned model, the machine-learned model configured to use the first optical data and the first ultrasound data as inputs
1106

Cause the combined ocular data to be displayed on a display device
1108

(51) Int. Cl.
    *G16H 50/20*      (2018.01)
    *G16H 50/30*      (2018.01)

(56)                  References Cited

U.S. PATENT DOCUMENTS

| | | | |
|---|---|---|---|
| 2014/0009741 A1* | 1/2014 | Levien | A61B 8/4281 |
| | | | 351/246 |
| 2016/0157817 A1* | 6/2016 | Tanassi | A61B 8/4281 |
| | | | 600/452 |
| 2020/0178936 A1* | 6/2020 | Padwal | A61B 5/4312 |
| 2021/0204906 A1* | 7/2021 | Giphart | A61B 8/5207 |
| 2022/0031165 A1* | 2/2022 | Courtney | G10K 11/002 |
| 2023/0329909 A1* | 10/2023 | Morely | G16H 20/40 |
| 2024/0008811 A1* | 1/2024 | Sassu | A61B 3/16 |

OTHER PUBLICATIONS

J. Park et al, "Quadruple ultrasound, photoacoustic, optical coherence, and fluorescence fusion imaging with a transparent ultrasound transducer", Proceedings of the National Academy of Sciences (PNAS), vol. 118, No. 1, pp. 1-12, Mar. 2021 (Year: 2021).*

* cited by examiner

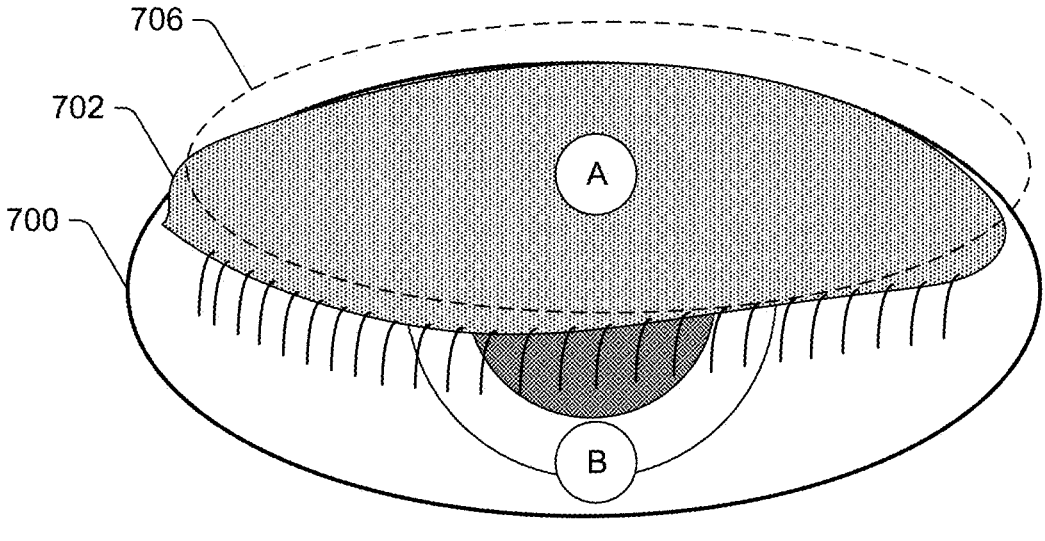
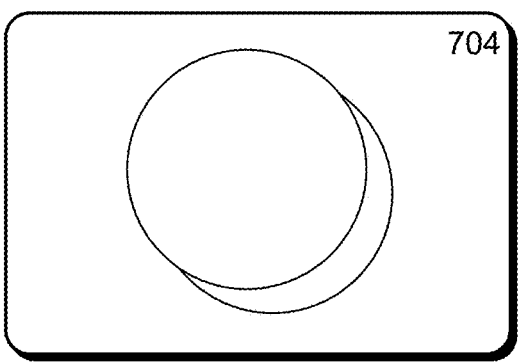
*Fig. 7*

800

900

1100

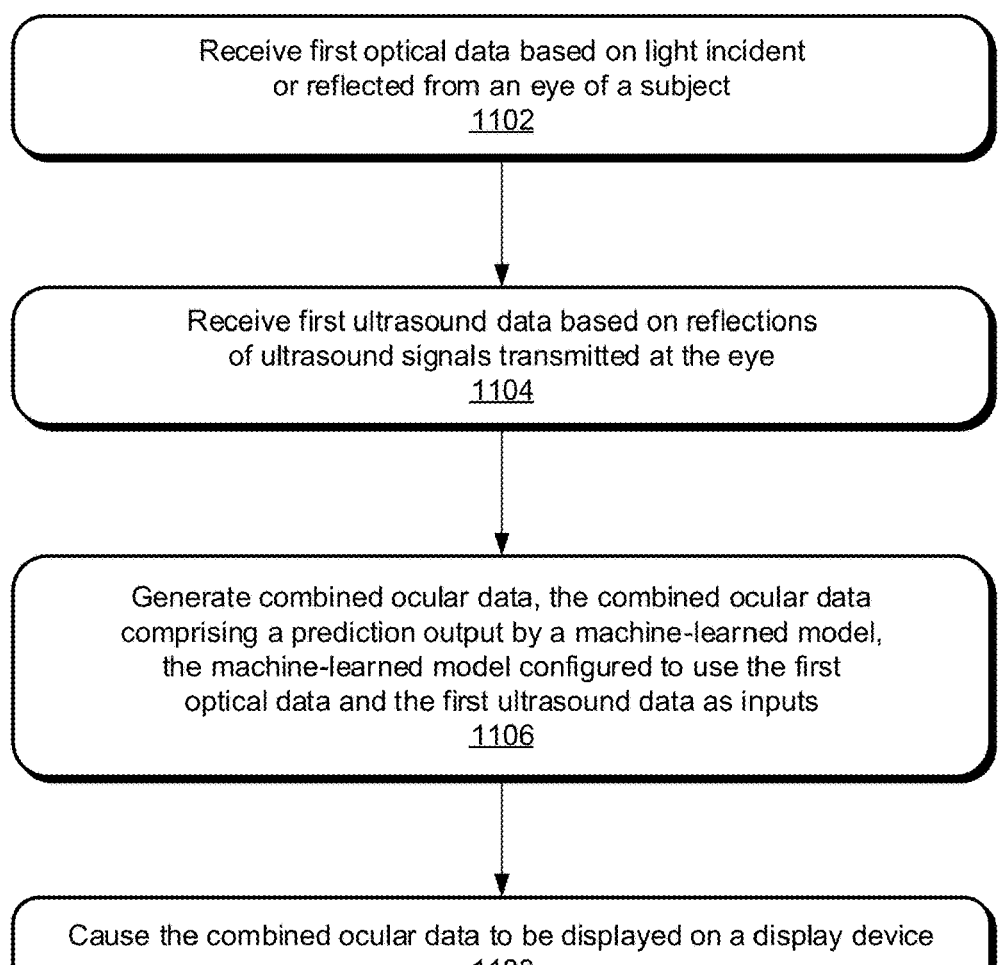

Receive first optical data based on light incident
or reflected from an eye of a subject
1102

Receive first ultrasound data based on reflections
of ultrasound signals transmitted at the eye
1104

Generate combined ocular data, the combined ocular data
comprising a prediction output by a machine-learned model,
the machine-learned model configured to use the first
optical data and the first ultrasound data as inputs
1106

Cause the combined ocular data to be displayed on a display device
1108

Figure 12:
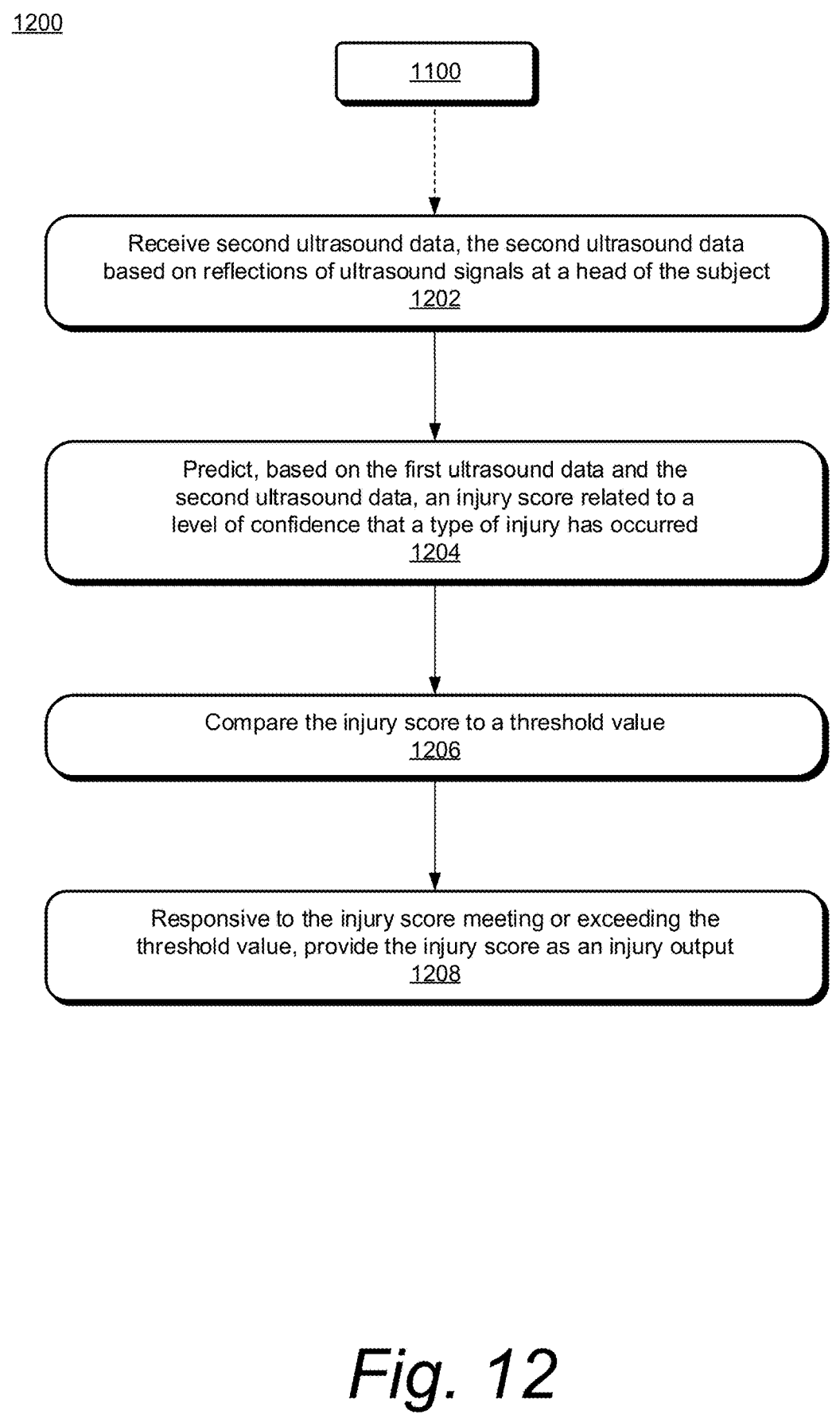

Receive second ultrasound data, the second ultrasound data
based on reflections of ultrasound signals at a head of the subject
1202

Predict, based on the first ultrasound data and the
second ultrasound data, an injury score related to a
level of confidence that a type of injury has occurred
1204

Compare the injury score to a threshold value
1206

Responsive to the injury score meeting or exceeding the
threshold value, provide the injury score as an injury output
1208

Figure 13:
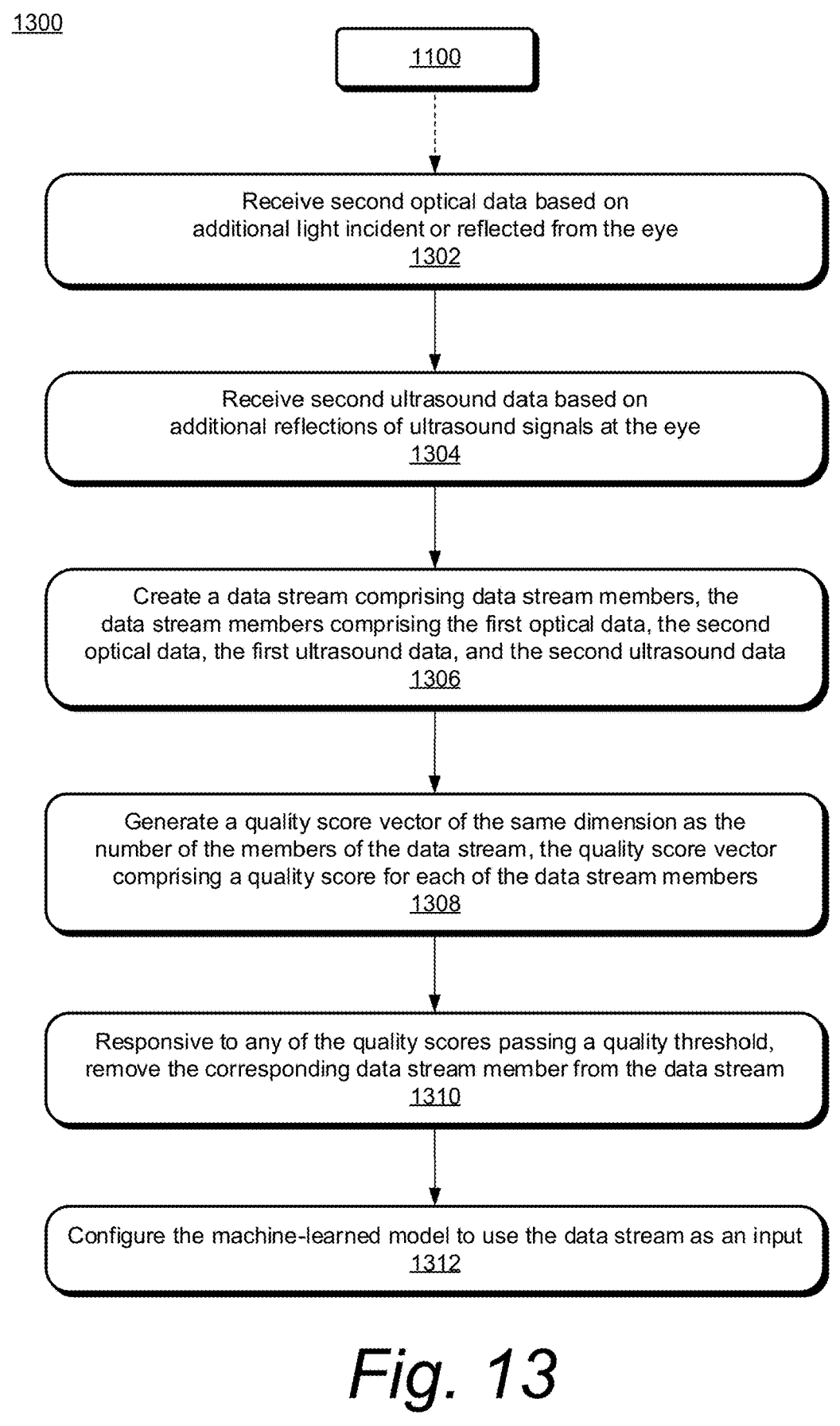

Receive second optical data based on
additional light incident or reflected from the eye
1302

Receive second ultrasound data based on
additional reflections of ultrasound signals at the eye
1304

Create a data stream comprising data stream members, the
data stream members comprising the first optical data, the second
optical data, the first ultrasound data, and the second ultrasound data
1306

Generate a quality score vector of the same dimension as the
number of the members of the data stream, the quality score vector
comprising a quality score for each of the data stream members
1308

Responsive to any of the quality scores passing a quality threshold,
remove the corresponding data stream member from the data stream
1310

Configure the machine-learned model to use the data stream as an input
1312

COMBINATION OCULAR ULTRASOUND AND OPHTHALMOSCOPE

BACKGROUND

Ultrasound devices can generate ultrasound images by transmitting sound waves at frequencies above the audible spectrum into a body, receiving echo signals caused by the sound waves reflecting from internal body parts, and converting the echo signals into electrical signals for image generation. Because they are non-invasive and non-ionizing, ultrasound devices are used ubiquitously. One example includes an ocular ultrasound device that can be used at the bedside to help differentiate between various ophthalmologic emergencies. However, an ocular ultrasound device is not always readily available in emergency care, and interpretation of ultrasound images of the eye requires specific training and expertise beyond that of a typical sonographer. Moreover, most ocular ultrasound devices require a patient's eye to be closed and covered in acoustic gel during an ocular examination.

In contrast, an ophthalmoscope, or its digital equivalent referred to as a fundus camera, can be used to generate optical images of an eye and is used when the patient's eye is open. However, to increase a window size of the eye that the ophthalmoscope images through, the patient's eye is usually dilated. This dilation is invasive and time-consuming to both induce before examination and recede after the examination is performed. Hence, ocular examinations may be uncomfortable for the patient, and the patient may not receive the best care possible.

SUMMARY

Devices and methods for a combination ocular ultrasound and ophthalmoscope are described. In some implementations, a combination ocular ultrasound and ophthalmoscope device (optical-ultrasound hybrid device) generates first ultrasound data from an ultrasound scan of an eye of a user using a first ultrasound scanner and generates optical data from an optical scan of the eye of the user using an optical sensor. The optical-ultrasound hybrid device generates an ultrasound image from the first ultrasound data and an optical image from the optical data. The optical-ultrasound hybrid device can further generate second ultrasound data using a second ultrasound sensor. The optical-ultrasound hybrid device can predict an injury score based on the first ultrasound data, the optical data, and/or the second ultrasound data. A hybrid image can be generated by the optical-ultrasound hybrid device from the first ultrasound data and the optical data, the hybrid image generated through the use of a machine-learned model. The optical-ultrasound hybrid device can increase diagnosis confidence, injury identification, and patient comfort and experience in comparison to conventional, disconnected ultrasound and ophthalmoscope systems and devices.

In some aspects, an optical-ultrasound hybrid device is disclosed. The optical-ultrasound hybrid device includes a housing, a first ultrasound scanner coupled to the housing, the first ultrasound scanner configured to generate first ultrasound data, the first ultrasound data based on reflections of ultrasound signals transmitted by the first ultrasound scanner at an eye of a subject, an optical sensor coupled to the housing, the optical sensor configured to generate optical data, the optical data based on light incident or reflected from the eye, one or more processors within the housing, and a memory within the housing, the memory storing instructions that, when executed by the one or more processors, cause the one or more processors to generate an ultrasound image based on the first ultrasound data and generate an optical image based on the optical data.

In some aspects, an ultrasound device is disclosed. The ultrasound device includes a housing, an ultrasound scanner coupled to the housing, the ultrasound scanner configured to generate first ultrasound data, the first ultrasound data based on reflections of ultrasound signals transmitted by the ultrasound scanner at an eye of a subject, one or more processors coupled to the housing, and a memory coupled to the housing, the memory storing instructions that, when accessed by the one or more processors, cause the one or more processors to receive the first ultrasound data and generate, using a machine-learned model that uses the first ultrasound data as an input, an optical image, the optical image generated in a style corresponding to an image produced by an optical sensor.

In some aspects, a method for generating an ocular output is disclosed. The method includes receiving first optical data based on light incident or reflected from an eye of a subject, receiving first ultrasound data based on reflections of ultrasound signals transmitted at the eye, generating combined ocular data, the combined ocular data comprising a prediction output by a machine-learned model, the machine-learned model configured to use the first optical data and the first ultrasound data as inputs, and causing the combined ocular data to be displayed on a display device.

Other devices and methods to provide an optical-ultrasound hybrid are also described. These other devices and methods, in addition to those already disclosed, may be combined to generate additional devices and methods, which, though not explicitly disclosed herein, still are the same in concept as the devices and methods described explicitly herein. The devices and methods explicitly outlined herein are meant to be illustrative and not limiting.

BRIEF DESCRIPTION OF THE DRAWINGS

The appended drawings illustrate examples and are, therefore, exemplary embodiments and not considered to be limiting in scope.

FIG. 6 illustrates an aligning/registration element of an optical-ultrasound hybrid device.

FIG. 7 depicts an anatomy to be scanned by an optical-ultrasound hybrid device and a gel-pad.

FIG. 11 illustrates an example method of an optical-ultrasound hybrid.

FIG. 12 illustrates the example method of FIG. 11 with additional operations.

FIG. 13 illustrates the example method of FIG. 11 with additional operations.

DETAILED DESCRIPTION

Figure 1:
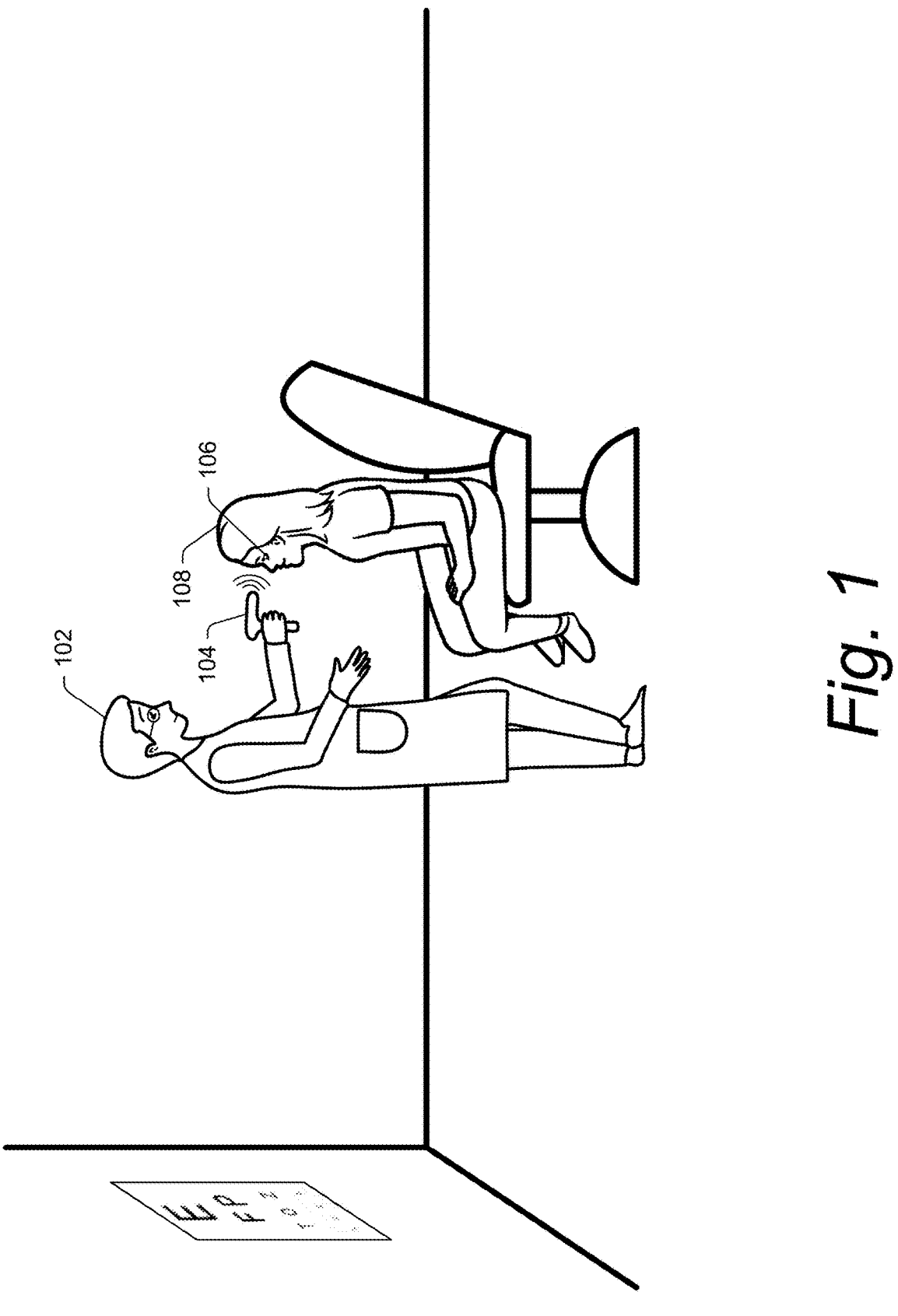
FIG. 1 illustrates an example environment for an optical-ultrasound hybrid device in accordance with one or more implementations.

Conventional ocular examinations use an ocular ultrasound system to generate ultrasound images or use an ophthalmoscope (or its digital equivalent, a fundus camera) to generate optical images. The ocular examination can be invasive and/or uncomfortable to the patient, and interpretation of the imaging results can require study by a specially trained clinician, who may not be available at the time of the examination. Moreover, an ocular ultrasound system and an ophthalmoscope cannot be concurrently used during a conventional examination since the ocular ultrasound system is used when a patient's eye is closed and covered in acoustic gel and the ophthalmoscope is used when the patient's eye is open and dilated. Hence, patients may not receive the best care possible.

Accordingly, devices and techniques are disclosed herein for an optical-ultrasound hybrid. In some implementations, the device can combine an ophthalmoscope or fundus camera with a miniaturized and dedicated ocular ultrasound device so that ultrasound can always be available during the ocular examination. Because low power may be required to avoid injury to the eye, a miniaturized and dedicated ocular ultrasound instrument can be implemented. One embodiment includes an optical ophthalmoscope with an attached ultrasound probe and embedded ultrasound front end with Bluetooth connection to a smartphone. Another embodiment includes a combination of a fundus camera with an ocular ultrasound using a single on-device display for both modalities. Another embodiment includes a patient-worn device including a combination of a fundus camera with an ocular ultrasound. The device can, in aspects, include a registration system that registers, or aligns, optical and ultrasound images for enhanced display. Hence, the examination can be automated, according to some implementations, by mechanically moving or electronically steering an ultrasound probe and/or moving an optical camera (e.g., ophthalmoscope, fundus camera, etc.). The device can include a machine-learned model (e.g., artificial intelligence) to assist with diagnosis with input from both modalities, to create combined imagery with input from both modalities, to create imagery from one modality in the style of the other modality (e.g., create an optical-style image of the eye from ultrasound data of the eye, etc.), or any combination of these facets. In this way, an ocular ultrasound can, according to some examples, function as an optical-ultrasound hybrid device by the production of optical-style imagery from the ultrasound data.

In an example, the optical-ultrasound hybrid device includes one or more machine-learned (ML) models (e.g., neural networks, clustering algorithms, etc.) that are implemented to process ultrasound data (e.g., ultrasound image, data representing the ultrasound image, etc.) and ophthalmoscope data (e.g., optical image of the eye, data representing the optical image of the eye, etc.), to combine the ultrasound data and ophthalmoscope data into a single image, to use the ultrasound data to generate one or more of an ultrasound image and an image in the style of an optical/ophthalmoscope image, to generate predictions of injury possibilities, or any number of other uses. Some example ML models are described relative to FIG. 9.

The optical-ultrasound hybrid device, according to some examples, additionally comprises a gel or gel-pad distribution mechanism. In some implementations, the gel-pad distribution mechanism can be configured to distribute a gel or other acoustic substance automatically or otherwise autonomously to an eyelid of an eye of a user to facilitate an ultrasound scan of the eye. According to some embodiments, the gel or gel-pad distribution mechanism requires manual deployment of the gel or gel-pad. The gel-pad distribution mechanism can house multiple gel-pads (or similar) and can be used multiple times without having to refill the gel-pad.

In one example, the optical-ultrasound hybrid device comprises an additional ultrasound scanner, the additional ultrasound scanner configured to scan a portion of the user's head that is not the eye of the user to generate second or additional ultrasound data. The additional ultrasound data can be combined with initial ultrasound data of the user's eye and optical data and used as an input to an ML model. The ML model can provide a prediction of an injury likelihood percentage, or some other metric associated with the likelihood of an injury to the user. The injury can be, for example, a head injury, such as a concussion. According to some implementations, the ML model can compare an injury score prediction to a threshold value and, if the injury score prediction value exceeds the threshold value, provide an output of the injury score prediction. Additional details of this example are provided later in this disclosure.

The optical-ultrasound hybrid device, according to some examples, additionally comprises a registration system. In some aspects, the registration system can track a movement of the eye of the user and adjust, based on the movement, at least one of an ultrasound position of the ultrasound scanner or an optical position of the ophthalmoscope (e.g., adjusting a position of an optical sensor used in the ophthalmoscope, etc.). The registration system will be discussed in greater detail later in this disclosure.

In one example, the optical-ultrasound hybrid device can be a wearable device. It can be possible, in aspects, for the wearable device to operate completely autonomously; that is, the wearable device can perform the ultrasound scan and the optical scan without input from an operator. This autonomous operation can also include the distribution of the gel-pad, as described herein, as well as the removal of the gel-pad or similar acoustic material used to facilitate an ultrasound scan.

These are a few of many possible example uses of the techniques described herein. Other example uses of the techniques described herein include, but are not limited to, at-home scanning, additional disease and injury diagnosis, and additional style types for image generation.

Combination Ultrasound and Ophthalmoscope Devices

FIG. 1 illustrates an example environment 100 for an optical-ultrasound hybrid device in accordance with one or more implementations. The environment 100 can be, for example, an optometrist office or some other area in which an ocular examination can be administered. An operator 102 may use an optical-ultrasound hybrid device 104 to administer an ocular examination of a patient 108, particularly of an eye 106 of the patient 108. According to one embodiment, the optical-ultrasound hybrid device 104 scans the eye 106 using both ocular ultrasound and ophthalmoscope techniques and probes. In some instances, a combination optical ultrasound and ophthalmoscope can implement one or more ML models to process ultrasound data and optical data generated by an ultrasound scanner and an optical sensor, respectively. The ultrasound scanner, according to one embodiment, can produce the ultrasound data based on reflections of ultrasound signals transmitted by the ultrasound scanner at the eye 106 of the patient 108. According to some examples, the optical sensor can be part of the ophthalmoscope and can generate the optical data based on light incident or reflected from the eye.

The ophthalmoscope/optical sensor and the ultrasound scanner can, in aspects, both be housed in the optical-ultrasound hybrid device 104. The device 104 can, for example, house an additional ultrasound scanner intended to produce second ultrasound data based on an ultrasound scan of a portion of the patient's 108 head that is not the eye 106. In some embodiments, the second ultrasound data can be used by the ML model along with the ultrasound data and/or the optical data to provide an output, such as a prediction of an injury to the patient 108 or an injury score that represents a probability or likelihood that an injury has occurred. The injury score, for example, can be compared to a threshold value, and if the injury score exceeds the threshold value, the ML model can provide an output of the injury score. The output may, in aspects, be an indication that the injury is present in the patient 108. According to some embodiments, the injury score can be a multi-dimensional vector, with each member of the multi-dimensional vector representing an individual injury score for a particular type of injury. In this way, the injury score output can include more than one member.

Figure 2:
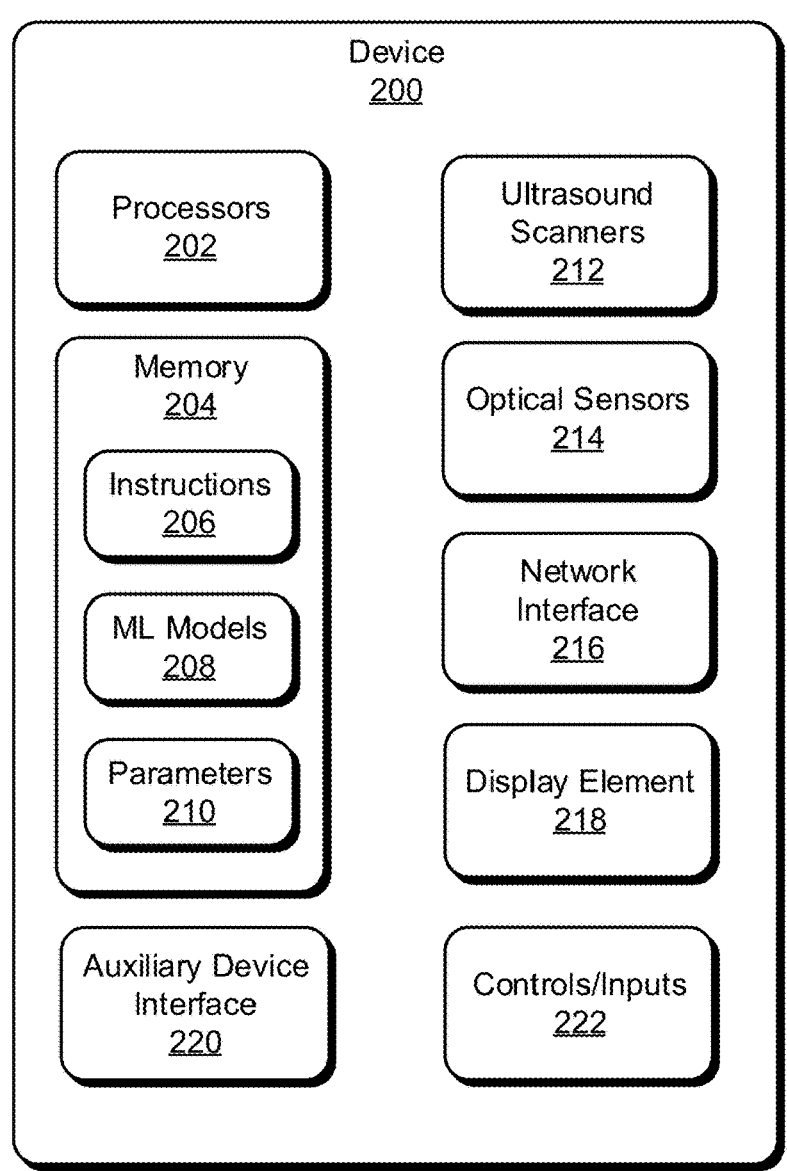
FIG. 2 illustrates a block diagram of an example computing device that can perform one or more of the operations described herein, in accordance with some implementations.

FIG. 2 illustrates a block diagram of an example computing device 200 that can perform one or more of the operations described herein, in accordance with some implementations of the optical-ultrasound hybrid device 104. The device 200 can, for example, include one or more processors 202 (e.g., a general-purpose processor, a PLD, etc.), a memory 204 (e.g., synchronous dynamic random-access memory (DRAM), read-only memory (ROM), flash memory, a data storage device, etc.) storing one or more of instructions 206, ML models 208, and other parameters 210, one or more ultrasound scanners 212, one or more optical sensors 214, a network interface 216, a display element 218 (e.g., a liquid crystal display (LCD), organic light-emitting diode (OLED), cathode ray tube (CRT), etc.), an auxiliary device interface 220, and controls/inputs 222 (e.g., an alphanumeric input such as a keyboard, a cursor control such as a mouse, a touch-screen input such as a digitizer, etc.). The one or more processors 202 can be, in an illustrative example, a complex instruction set computing (CISC) microprocessor, a reduced instruction set computing (RISC) microprocessor, a very long instruction word (VLIW) microprocessor, or a processor implementing other instruction sets or processors implementing a combination of instruction sets. According to some implementations, the one or more processors 202 can also comprise one or more special-purpose processors such as an application-specific integrated circuit (ASIC), a field programmable gate array (FPGA), a digital signal processor (DSP), a network processor, or the like.

Not all elements of the device 200 shown in FIG. 2 need to be implemented in a same housing. By way of example, the auxiliary device interface 220 can be used to couple with a mobile phone (not pictured), and the display element 218 can be a display of the mobile phone. Alternate embodiments using different combinations of the described elements are available and equivalent to those described specifically herein.

Figure 3:
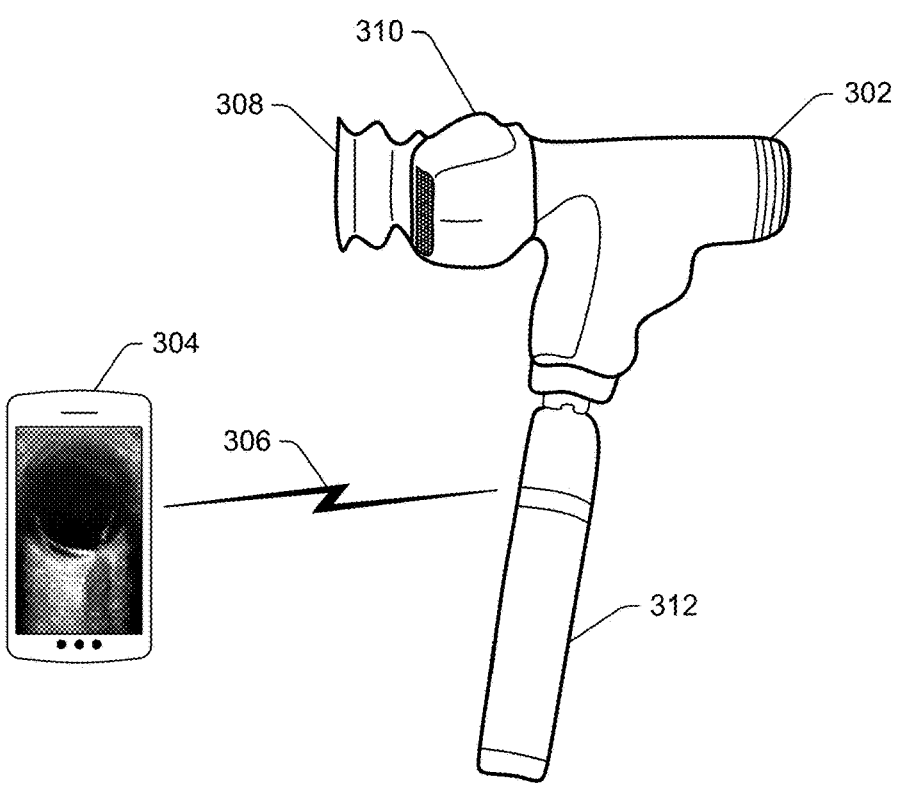
FIG. 3 illustrates an example optical-ultrasound hybrid device with a remote interface element.

FIG. 3 illustrates an example optical-ultrasound hybrid device 302 with a remote interface element, such as the device 200. According to some embodiments, a system 300 includes both the optical-ultrasound hybrid device 302 and a mobile device 304 connected over a wireless connection 306. In aspects, the optical-ultrasound hybrid device 302 and the mobile device 304 may be connected over a physical connection, such as a USB cable or other suitable, physical connection interface (not pictured). In some examples, the optical-ultrasound hybrid device 302 can include an optical sensor 308, an ultrasound scanner 310, and a handle 312. According to some embodiments, the optical sensor 308 and ultrasound scanner 310 can both be coupled to a same housing of the optical-ultrasound hybrid device 302. This coupling can enable an operator (e.g., operator 102, etc.) to scan an eye of a patient (e.g., eye 106 of patient 108, etc.) using either the optical sensor 308 or the ultrasound scanner 310. The optical sensor 308 and the ultrasound scanner 310, in some examples, can be able to rotate on the optical-ultrasound hybrid device 302, allowing for use of either the optical sensor 308 or the ultrasound scanner 310 by the operator. In some aspects, this rotation can be automated or otherwise actuated by a driven rotation mechanism (not pictured) or can be a manual rotation performed by the operator.

According to some implementations, the optical-ultrasound hybrid device 302 can output ultrasound data, optical data, or both to the mobile device 304. By way of example, an operator can perform an ultrasound scan on an eye of a patient. The ultrasound scan can use the ultrasound scanner 310, and the ultrasound scanner 310 can produce ultrasound data, which can be used to produce an ultrasound image. The ultrasound image, in some examples, can be sent over the wireless connection 306 to the mobile device 304, which can in turn output the ultrasound image. Additional imagery, such as an optical image based on optical data from the optical sensor 308, a hybrid image produced by an ML model and based on both the ultrasound data and the optical data, an optical-style image based on the ultrasound data, or any number of other image types, can be similarly sent to and displayed by the mobile device 304 according to some implementations.

Controls can be, according to some examples, implemented for operation of the optical-ultrasound hybrid device 302. These controls can be, for example, placed on the handle 312 or elsewhere on the optical-ultrasound hybrid device 302. These controls can be, by way of example, substantially the same as the controls/inputs 224 on the device 200 from FIG. 2. In some aspects, the controls can allow the operator to control which of the sensors, the ultrasound scanner 310 or the ophthalmoscope/optical sensor 308, is used to scan the eye of the patient. Additionally or alternately, the mobile device 304 can be, for example, used to control the optical-ultrasound hybrid device 302. By way of example, the mobile device 304 can be a mobile phone. The mobile device 304, according to some implementations, can have an application allowing for control of the optical-ultrasound hybrid device 302 over the wireless connection 306. In an alternate embodiment, the mobile device 304 can be a dedicated or proprietary device designed as a companion device to the optical-ultrasound hybrid device 302.

Figure 4:
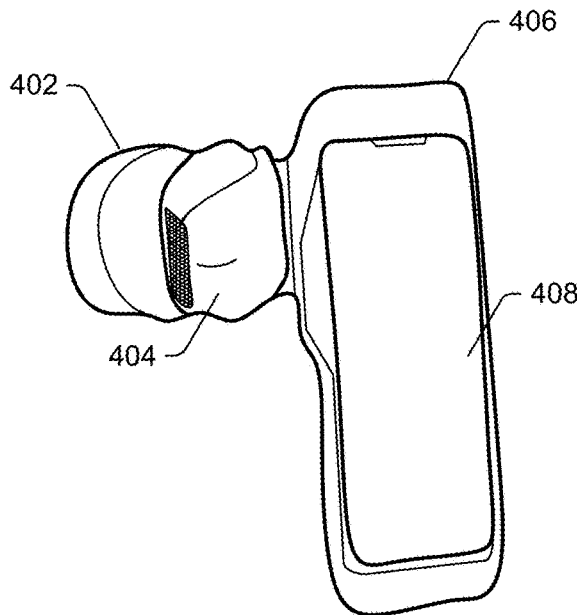
FIG. 4 illustrates an example implementation of an optical-ultrasound hybrid device with an auxiliary device.

FIG. 4 illustrates another example implementation of an optical-ultrasound hybrid device. A system 400 shows an optical sensor 402 and an ultrasound scanner 404 coupled to a housing 406 with a cavity, according to some implementations. The cavity, by way of example, can be used to house a display device 408. The display device 408 can be, for example, a smartphone. In this way, the housing 406 can comprise a mount for the display device 408, which can also be able to couple the display device 408 electronically. For example, the mount can include an electrical connector, which can allow the display device 408 to act as a controller for the optical sensor 402 and the ultrasound scanner 404. Additionally or alternatively, one or both of the optical sensor/ophthalmoscope 402 and the ultrasound scanner 404 can, by way of example, be electronically coupled to the display device 408 via a wireless communication link, such as a Bluetooth or Wi-Fi connection.

The display device 408 can, according to some examples, display images rendered from ultrasound data generated by the ultrasound scanner 404, such as an optical image rendered from optical data generated by the optical sensor 402, a hybrid image rendered from both the ultrasound data and the optical data, or another image type rendered from one or both of the ultrasound data and the optical data. According to some examples, such imagery can be a product of an ML model, where the model can take as inputs the ultrasound data, the optical data, or both.

The display device 408, for example, can also be able to control the ultrasound scanner 404 and the optical sensor 402. In some aspects, the display device 408 can be able to select between the ultrasound scanner 404 and the optical sensor 402, and the selection can be carried out by a mechanized selection feature of the system 400. The selection feature can be, in some examples, implemented by means of a motor. In aspects, the system 400 can have other features not pictured but outlined in this disclosure, such as a second ultrasound scanner and a gel-pad distribution mechanism.

Figure 5:
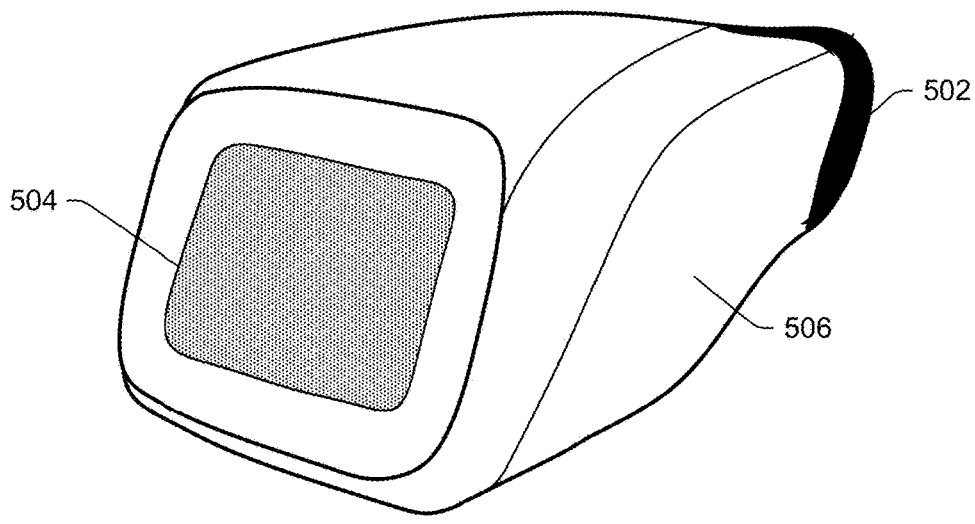
FIG. 5 illustrates another example implementation of an optical-ultrasound hybrid device.

FIG. 5 illustrates another example of an optical-ultrasound hybrid device. A device 500 can, by way of example, comprise a single housing 506, which houses all components necessary for the optical-ultrasound hybrid device. According to some implementations, the device 500 can have one or more sensors 502, which can be one or more ultrasound scanners and one or more optical sensors. The device 500 can also, in aspects, comprise a display and control interface 504, the display and control interface 504 able to display an output and comprising input controls and a display element. According to some examples, the input controls can be part of a virtual interface, such as one comprising a touchscreen. The device 500 can, for example, have other components not pictured, such as a gel-pad distribution mechanism.

The device 500 can, in some implementations, be a wearable device 500. This, for example, can be accomplished using a strap (not pictured) or other coupling mechanism to secure the device 500 to the head of a patient. In the wearable device 500 embodiment, it can be possible for the patient to self-administer an examination, in some instances, as operation of the wearable device 500 can be completely autonomous. According to some embodiments, the wearable device 500 can take minimal user input from a patient in order to administer an ocular examination. According to some embodiments, the wearable device 500 can be connected to a network and can send results of the examination over the network. The wearable device 500 can, by way of example, include a registration mechanism to register and account for movement of an eye of the patient, as described below.

Example Eye Movement Registration/Tracking Mechanism

In an example, a device, such as an optical-ultrasound hybrid device, can include a registration mechanism that can be used to determine relative positions of an ultrasound scanner of the device, an optical sensor (e.g., an ophthalmoscope and/or fundus camera, etc.) of the device, and an anatomy of a patient (e.g., a part of an eye of the patient, etc.). According to some embodiments, the device can use the registration mechanism to align an ultrasound image and/or an optical image. According to some implementations, the registration mechanism can include mechanical elements, which can be used to move and/or align the ultrasound scanner and the optical sensor.

Figure 6:
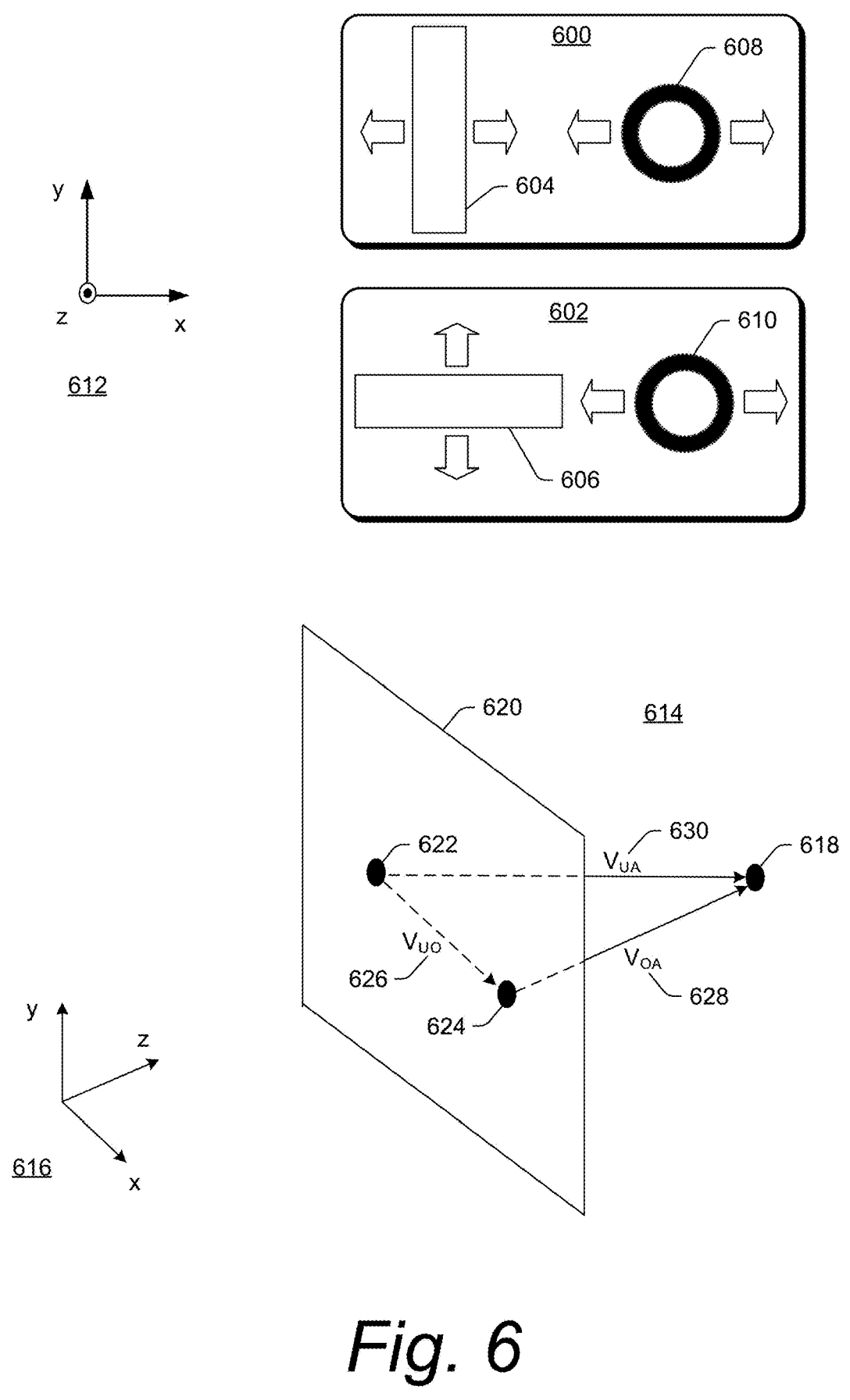

FIG. 6, for example, illustrates part of a registration system for an optical-ultrasound hybrid device in accordance with one or more implementations. In FIG. 6, two example layouts (layout 600, layout 602) are shown having different configurations of elements. In each of these examples, a transducer 604, 606 (e.g., ultrasound scanner/ probe, etc.) and a camera 608, 610 (e.g., optical sensor, fundus camera, ophthalmoscope, etc.) can move back and forth on rails to support automated alignment and scanning. The movement is illustrated by the arrows in the layouts 600, 602. According to some embodiments, this same mechanism can also support 3D scanning and registration of images. The transducer 604, 606 and/or camera 608, 610 can, for example, also be rotated to obtain orthogonal views. For instance, the rotation can be about an axis normal to the layouts 600, 602, such as in a coordinate system 612. In the coordinate system 612, there is an x-axis, a y-axis, and a z-axis. The x- and y-axes are on the page, and the z-axis is out of the page. The layout 600 shows the transducer 604 in a first configuration, with the layout 602 showing the transducer 606 in a configuration orthogonal to that of the transducer 604. It may be possible, by way of example, to change from the transducer orientation in layout 600 to that of layout 602 by rotating the transducer 604 about the z-axis by an angle of 90°. In some implementations, the transducer 604, 606 can be configured such that it is able to operate in both layouts 600 and 602.

The device can, according to some embodiments, include any suitable positioning system to determine relative positions in a coordinate system of the device. In aspects, the registration mechanism can determine a distance from a tip of the transducer 604, 606 to an anatomy, such as a retina, and this information can be combined with positioning data so that a position of the anatomy relative to the camera 608, 610 can also be determined. In one example, vector analysis can be employed to determine this distance. Consider a space 614, which can, for example, have a coordinate system 616, including an x-axis, a y-axis, and a z-axis. The space 614 can also include both an anatomy 618 and an optical-ultrasound hybrid device 620, including an ultrasound scanner 622 and an optical sensor 624. The optical-ultrasound hybrid device 620 has been simplified to a plane in FIG. 6 to illustrate a known geometric relationship between spatial positions of the ultrasound scanner 622 and the optical sensor 624. According to some embodiments, the optical-ultrasound hybrid device 620 does not have a planar arrangement in its housing, but a virtual plane can be constructed in space regardless, which can at least mathematically represent a spatial relationship between the ultrasound scanner 622 and the optical sensor 624. Other arrangements and spatial relationships can also be employed, such as spheres, cylinders, other geometric spatial relationships, etc. A vector $V_{UO}$ 626, by way of example, can be a known distance and direction between the ultrasound scanner 622 and the optical sensor 624 and can have x, y, and z coordinates. A distance and direction to the anatomy 618 can be found, for instance by the optical sensor 624, which in the example in FIG. 6 results in a known vector $V_{OA}$ 628. A distance and direction from the ultrasound scanner 622 to the anatomy 618, represented by a vector $V_{UA}$ 630, can then be found, for example via the formula $V_{UO}=V_{UA}-V_{OA}$, which can result in the ability to calculate the vector $V_{UA}$ 630. Other methods of calculating or otherwise determining the distances between the optical sensor 624 and the anatomy 618 and/or between the ultra-sound scanner 622 and the anatomy 618 can also be employed and are well known to a person of ordinary skill in the art.

By way of example, the registration mechanism can also be used in an examination where the ocular ultrasound scanner 604, 606, 622 and the optical sensor 608, 610, 624 (e.g., ophthalmoscope, fundus camera, etc.) are sequentially operated. The anatomy 618 of a patient can be, for example, an eye 618 of the patient. During the examination, the eye 618 of the patient may remain open and the optical sensor 608, 610, 624 can be moved, for example to generate an optical image of the eye 618 of the patient. In aspects, the registration mechanism can determine the position of the optical sensor 624 and can move the optical sensor 624 out of the way, enabling the ultrasound sensor 622 to be moved into a position where the ultrasound sensor 622 can generate an ocular ultrasound image. The patient may close their eye 618 during an ocular ultrasound portion of the examination, enabling a user of the optical-ultrasound hybrid device 620 to apply a gel-pad or similar acoustic coupling material (not shown) over the eye 618 of the patient to help facilitate the ocular ultrasound portion of the examination. Additionally or alternatively, the optical-ultrasound hybrid device 620 can, in aspects, automatically apply the acoustic coupling material, such as with a roller that positions the acoustic coupling material based on data from the registration mecha-nism.

According to some embodiments, the optical-ultrasound hybrid device 620 can use the registration mechanism to determine a position of the ultrasound scanner 604, 606, 622, which can provide relative positions of the ultrasound scanner 604, 606, 622 and the optical sensor 608, 610, 624 when they generate image data. Using landmarks in the eye 618 of the patient and corresponding positions, together with the relative positions of the ultrasound scanner 604, 606, 622 and the optical sensor 608, 610, 624, the registration mecha-nism can, for example, combine ultrasound data from the ultrasound scanner 604, 606, 622 and optical data from the optical sensor 608, 610, 624 to generate an inference. For instance, the registration mechanism can comprise a neural network or other ML model. According to some embodi-ments, the neural network can take the ultrasound data and the optical data as inputs and can generate the inference. Additionally or alternately, the optical-ultrasound hybrid device 620 can generate an ultrasound image, an optical image, or both from the ultrasound data and the optical data, respectively, and use the ultrasound image, the optical image, or both as inputs for the ML model/neural network. The neural network can additionally or alternately receive registration data. The ultrasound image, for example, can include a B-mode image (whose imaging plane can be generally orthogonal to the optical imaging plane) or a C-mode image (whose imaging plane can be generally parallel to the optical imaging plane). In an example, the ultrasound image can include an M-mode image, which can have a time-dependent component in the generation of the ultrasound image. The neural network can, in aspects, gen-erate any suitable inference, such as a segmentation, an identification, a classification, etc. In one example, the neural network can generate a 3D image based on one or more of the ultrasound data and the optical data. Additionally or alternatively, the neural network can generate a panoramic image. The panoramic image generated by the neural network can, in aspects, be more accurate than traditional methods of panoramic ultrasound image genera-tion as traditional methods do not have a mechanically controlled ultrasound scanner, as used with the registration mechanism, but such traditional methods instead employ a free-hand control.

The ultrasound image (e.g., that produced by the neural network, etc.) can be improved using the registration mecha-nism over a traditional method in part because the eye 618 of the patient can be moving during data capture. According to some embodiments, this movement of the eye 618 of the patient can be accounted for by the registration mechanism. According to some embodiments, registration data is com-bined with feature matching data of conventional/traditional methods to generate the ultrasound image, such as the panoramic image.

In one example, the device 620 can include a pre-processor that can determine, based on a quality check, whether to save or discard one or more of the ultrasound data and the optical data and/or whether to proceed to process the ultrasound data and the optical data with the ML model/ neural network. The patient can, by way of example, move their eye 618 during imaging, which can prompt the device 620 to determine that the ultrasound data, the optical data, or both do not meet a threshold quality value. According to some embodiments, the device 620 can then discard the ultrasound data, the optical data, or both, rather than save and process these data with a neural network. The device 620 can then, by way of example, prompt the user to generate one or more additional ultrasound data and/or additional optical data, automatically generate one or more additional ultrasound data and/or additional optical data, or some combination thereof.

Example Gel-Pad Distribution

FIG. 7 depicts an anatomy to be scanned by an optical-ultrasound hybrid device. In embodiments, rather than sequentially performing ocular ultrasound imaging and opti-cal imaging, the optical-ultrasound hybrid device can per-form simultaneous ocular ultrasound imaging with an ocular ultrasound scanner and optical imaging with an optical sensor (e.g., ophthalmoscope and/or fundus camera, etc.). An eye 700 of a user, for example, can have an eyelid 702. According to some embodiments, the ultrasound scanner can be placed over the upper (or lower) eyelid 702 while the eye 700 is partially open, and the optical sensor, which can include a camera lens, can be placed over the exposed part of the eye 700. FIG. 7 illustrates the eye 700 partially open, with the top eyelid 702 covering an upper portion of the eye 700. The optical-ultrasound hybrid device can, for example, comprise a gel-pad distribution mechanism, which can dis-tribute a gel-pad or similar acoustic coupling material onto the eyelid 702. Using the registration mechanism described above, the optical-ultrasound hybrid device (e.g., device 620) can, by way of example, accurately place the gel-pad or the similar acoustic coupling material on top of the exposed upper eyelid 702, such as with a roller or other mechanism suitable to distribute the gel-pad or the similar acoustic coupling material. In aspects, the optical-ultrasound hybrid device can simultaneously scan a region marked "A" with the ultrasound scanner and capture an image of a region marked "B" with the optical sensor. Additionally or alter-natively, the device can, for example, first scan the region marked "A" with the ultrasound scanner and then capture an image of the region marked "B" with the optical sensor. According to some embodiments, the device can first capture an image of the region marked "B" with the optical sensor and then scan the region marked "A" with the ultrasound scanner.

In an example, the gel-pad distribution mechanism can include a compensation system, which can store or determine optical properties of the gel-pad or the acoustic coupling material. Hence, an example system of this type can generate an optical image with the optical sensor through the acoustic coupling material, such as in the region "A" of FIG. 7. According to some examples, the compensation system can then use the stored optical properties to invert (or compensate for or equalize) the optical image to remove loss or distortion that can be caused by light moving through the acoustic coupling material.

An example of the gel-pad or the acoustic coupling material 704 is shown in FIG. 7. According to some examples, the acoustic coupling material 704 can comprise a gel-pad portion attached to a secondary material. The gel-pad portion of the acoustic coupling material 704 can, in aspects, be a very soft, pliable gel-filled pillow/disk, and the disk can be sized to fit inside a cup on a patient-facing end of the optical-ultrasound hybrid device and can be configured such that it can easily conform to an eyeball shape to prevent undue pressure against the eye 700 or eyelid 702. A position of the acoustic coupling material 704 can, for example, be represented by an area 706 encompassed by the dashed line. According to some embodiments, the acoustic coupling material 704 can permit movement of the ultrasound scanner without requiring an obtrusive or otherwise unpleasant amount of acoustic gel on the eyelid 702, such as what can be used in conventional ocular ultrasound systems.

Example Machine-Learned Models

Figure 8:
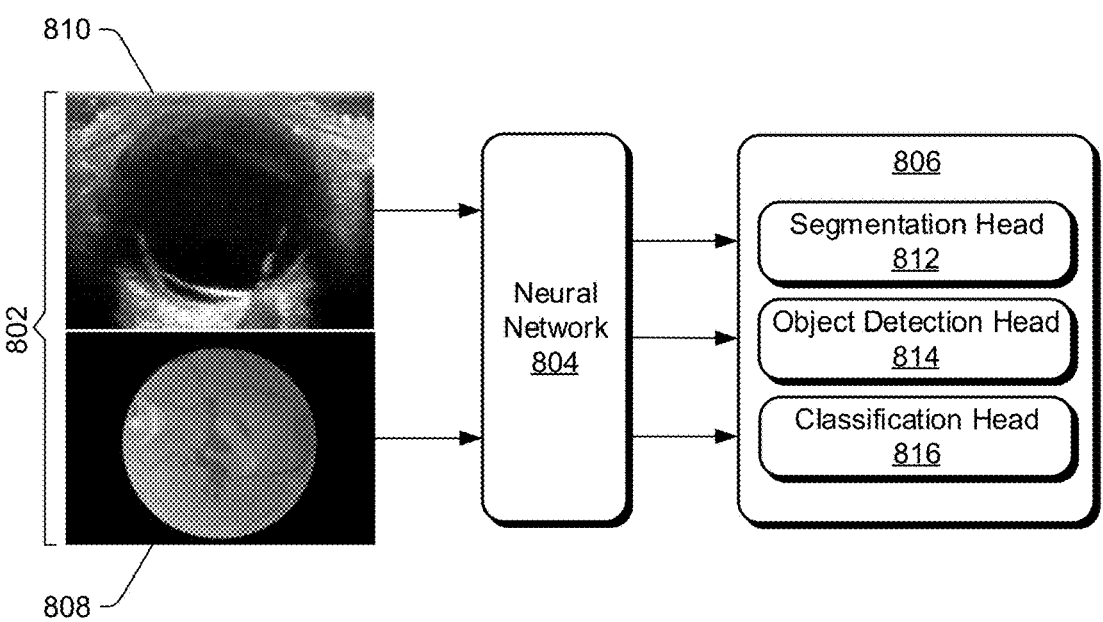
FIG. 8 represents an example machine-learned model processing of input from an optical-ultrasound hybrid device.

FIG. 8 represents an example ML model processing of an input from an optical-ultrasound hybrid device. In aspects, an ML model 800 can include inputs 802, a neural network 804, and a generation module 806. The inputs 802 can, by way of example, comprise optical data and ultrasound data, which can be used to generate an optical image 808 and an ultrasound image 810. Additionally or alternately, the optical image 808 and the ultrasound image 810 can, in aspects, be used as the inputs 802 for the ML model 800. According to some implementations, the generation module 806 can comprise a segmentation head 812, an object detection head 814, a classification head 816, or more or fewer components. The segmentation head 812 can, in some examples, highlight structures of interest in the inputs 802, such as by generating segmentations of the structures, segmentation images, etc. According to some embodiments, the object detection head 814 can generate bounding boxes of structures of interest in the inputs 802. The classification head 816 can, for example, indicate suspected pathologies from the inputs 802.

The inputs 802 can, in some implementations, be input as data, such as a matrix or other, multi-dimensional mathematical object. In aspects, the neural network 804 can include a feature-extraction component, such as a convolutional neural network (CNN). The neural network 804 can, in some examples, comprise several different neural network architectures known to a person of ordinary skill in the art and can comprise any combination of like or different architectures. According to some embodiments, the neural network 804 can comprise a single architecture type. These example neural network architectures and combinations are listed as examples only and are not meant to limit the scope of the neural network 804. It should be noted that the neural network 804, for example, can comprise other than a learning network, as can be construed by the term "neural network." Rather, in aspects the neural network 804 can comprise an algorithm derived from a machine-learning training, as is explained below.

Many of the aspects described herein can be implemented using an ML model. For the purposes of this disclosure, an ML model is any model that accepts an input, analyzes and/or processes the input based on an algorithm derived via machine-learning training, and provides an output. An ML model can be conceptualized as a mathematical function of the following form:

$$f(\hat{s}, \theta) = \hat{y} \qquad \text{Equation (1)}$$

In Equation (1), the operator f can represent the processing of the ML model based on an input and providing an output. The term $\hat{s}$ can represent a model input, such as ultrasound data, optical data, or both or other data. The ML model can analyze/process the input $\hat{s}$ using parameters $\theta$ to generate an output $\hat{y}$ (e.g., object identification, object segmentation, object classification, etc.). Both the input $\hat{s}$ and the output $\hat{i}$ can be scalar values, matrices, vectors, or mathematical representations of phenomena such as categories, classifications, image characteristics, the images themselves, text, labels, or the like. The parameters $\theta$ can be any suitable mathematical operations, including but not limited to applications of weights and biases, filter coefficients, summations or other aggregations of data inputs, distribution parameters such as mean and variance in a Gaussian distribution, linear algebra-based operators, or other parameters, including combinations of different parameters, suitable to map data to a desired output.

Figure 9:
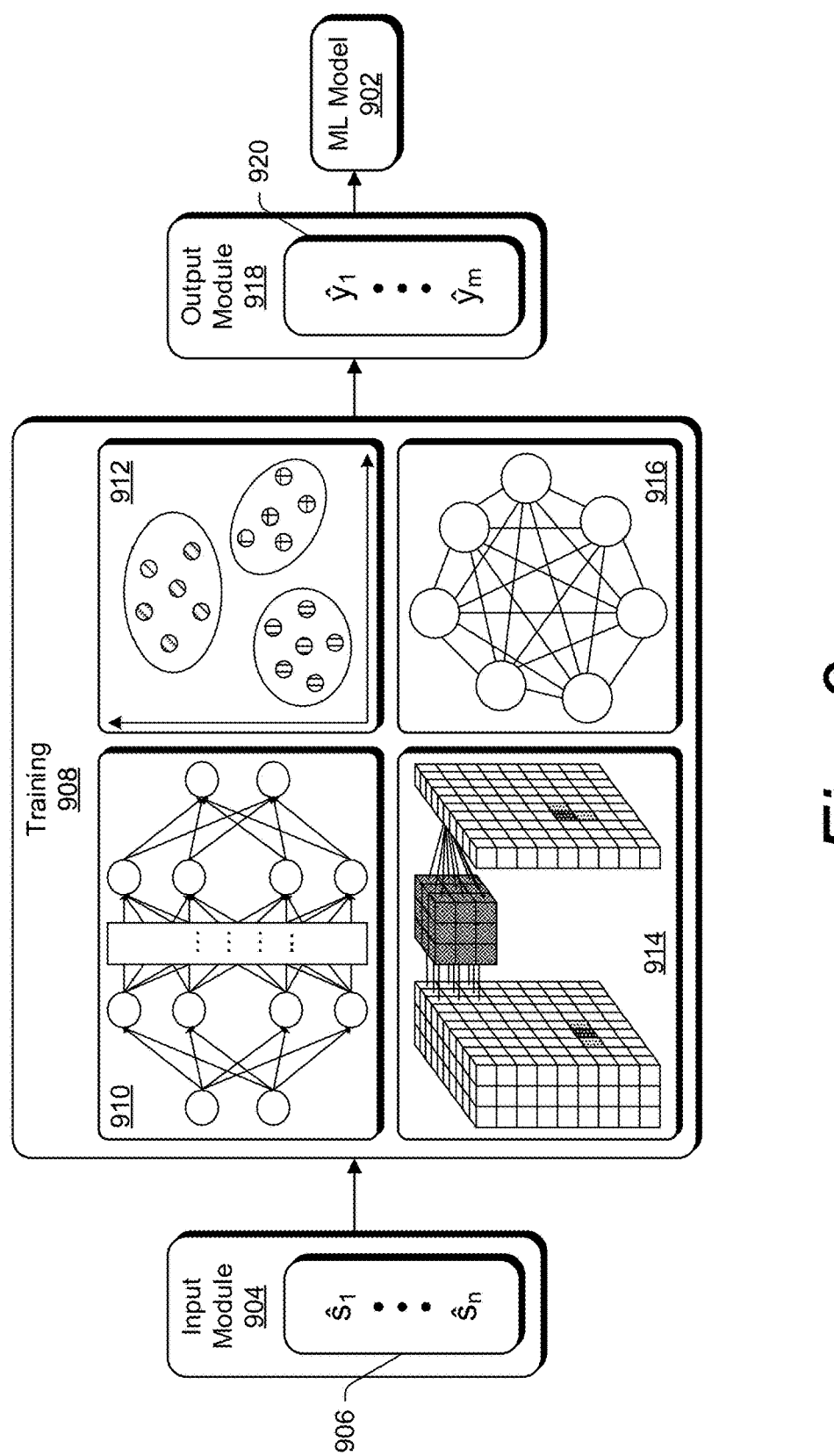
FIG. 9 represents an example machine-learning architecture used to train a machine-learned model.

FIG. 9 represents an example machine-learning architecture 900 used to train an ML model 902 (e.g., machine-learned model 800). An input module 904 can accept an input s 906, which can be an array with members $\hat{s}_1$ through $\hat{s}_n$. The members of the array can be multidimensional, or the array itself can instead be a matrix or other mathematical object holding multiple points or vectors of data values. The input $\hat{s}$ 906 can be fed into a training module 908, which can process the input $\hat{s}$ 906 based on the machine-learning architecture 900. For example, if the machine-learning architecture 900 uses a multilayer perceptron (MLP) model 910, the training module 908 applies weights and biases to the input $\hat{s}$ 906 through one or more layers of perceptrons, each perceptron performing a fit using its own weights and biases according to its given functional form. The MLP weights and biases can be adjusted such that they are optimized against a least mean square, logcosh, or other optimization function (e.g., loss function, etc.) known in the art. Although the MLP model 910 is described here as an example, any suitable machine-learning technique can be employed, some examples of which include but are not limited to k-means clustering 912, convolutional neural networks (CNN) 914, a Boltzmann machine 916, a Gaussian mixture model (GMM), and a long short-term memory (LSTM). The training module 908 can provide an input to an output module 918. The output module 918 can analyze the input from the training module 908 and provide an output in the form of $\hat{y}$ 920, which can be an array with members $\hat{y}_1$ through $\hat{y}_m$, or another single- or multiple-dimensional object. The output $\hat{y}$ 920 can represent a known correlation with the input $\hat{s}$ 906, such as, for example, object identification, segmentation, and/or classification.

In some examples, the input $\hat{s}$ 906 can be a training input labeled with known output correlation values, and these known values can be used to optimize the output $\hat{y}$ 920 in training against the optimization/loss function. In other examples, the machine-learning architecture 900 can categorize the output $\hat{y}$ 920 values without being given known correlation values to the inputs $\hat{y}$ 906. In some examples, the machine-learning architecture 900 can be a combination of machine-learning architectures. By way of example, a first network can use the input $\hat{s}$ 906 and provide the output $\hat{y}$ 920 as an input $\hat{s}_{ML}$ to a second machine-learned architecture, with the second machine-learned architecture providing a final output $\hat{y}^f$. In another example, one or more machine-learning architectures can be implemented at various points throughout the training module 908.

In some machine-learned models, all layers of the model can be fully connected. For example, all perceptrons in the MLP model 910 act on every member of s. For the MLP model 910 with a 100×100 pixel image as an input, each perceptron provides weights/biases for 10,000 inputs. With a large, densely layered model, this can result in slower processing and/or issues with vanishing and/or exploding gradients. The CNN 914, which can, in some constructions, not be a fully connected model, can process the same image using 5×5 tiled regions, requiring only 25 perceptrons with shared weights, giving much greater efficiency than the fully connected MLP model 910. Additionally or alternately, the training module 908 can employ sections of architecture that are fully connected and sections that are not. By way of example, the input $\hat{s}$ 906 can be a matrix representing data from both an ultrasound image and an optical image and the training module 908 can use the CNN 914 to identify features from the input $\hat{s}$ 906. The features can then be used as auxiliary inputs for the MLP model 910, which can subsequently give an output to the output module 918. The CNN 914 portion of this example is not fully connected, but the MLP 910 portion is fully connected, where every perceptron in a first layer takes every input from the CNN 914 and all perceptrons are causally connected to the eventual input for the output module 918. Other architecture types and combinations can be employed by a person of ordinary skill in the art, and the foregoing example is not meant to be limiting, but illustrative.

Figure 10:
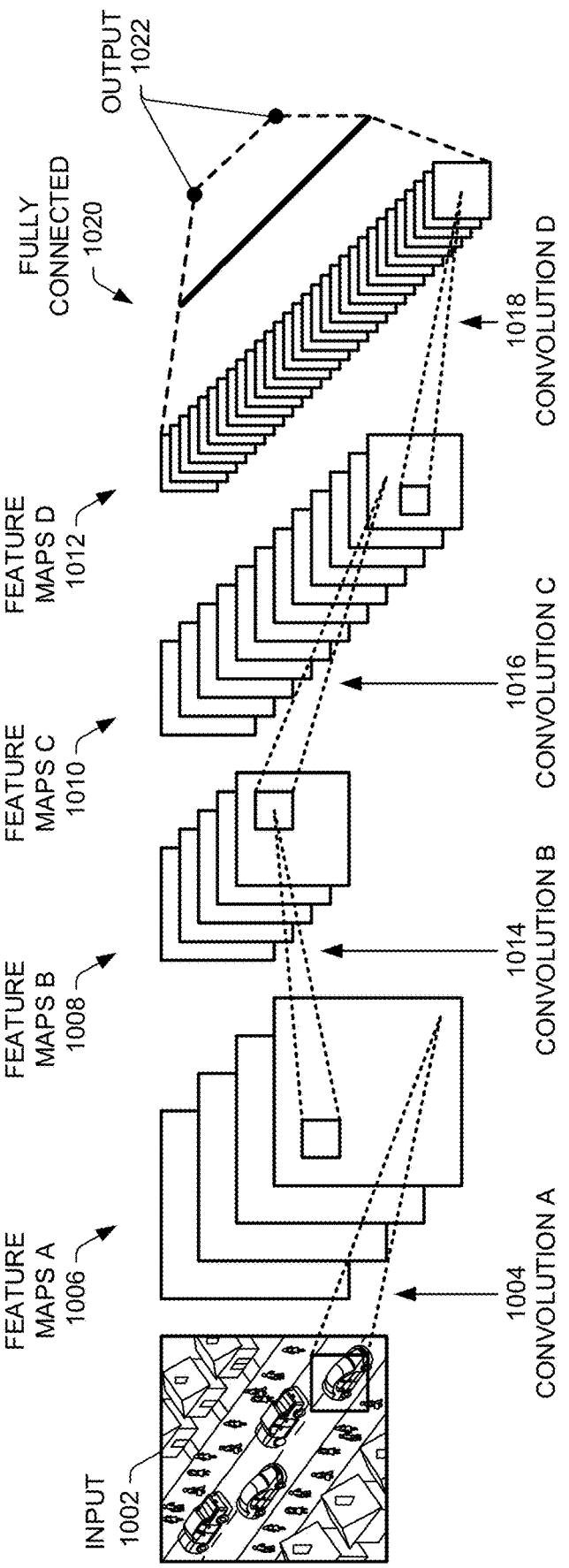
FIG. 10 represents an example model using a convolutional neural network to process an input image.

FIG. 10 represents an example model 1000 using a CNN to process an input image 1002, which can include representations of objects that can be identified via object recognition, such as people or cars (or an anatomy, such as the eye 700, etc.). Convolution A 1004 can be performed, for example, to create a first set of feature maps (e.g., feature maps A 1006, etc.). A feature map can be a mapping of aspects of the input image 1002 given by a filter element of the CNN. This process can be repeated using, by way of example, feature maps A 1006 to generate further feature maps B 1008, feature maps C 1010, and feature maps D 1012 using convolution B 1014, convolution C 1016, and convolution D 1018, respectively. In this example, feature maps D 1012 can become an input for fully connected network layers 1020. In this way, the ML model 1000 can be trained to recognize certain elements of the image, such as people, cars, or a particular patient anatomy, and provide an output 1022 (e.g., a prediction, inference, etc.) that, for example, can identify the recognized elements. By way of example, an ultrasound image of an eye can have certain nonconformities that can be tumors. These tumors can be selected as features in the CNN at, for instance, convolution B 1014 and thus can be used as inputs via feature maps B 1008. Other features, either normally found in the eye, abnormally found in the eye, or otherwise, can also be determined to be features by the CNN in this example. Additionally or alternately, each feature map, such as feature maps C 1010, can contain multiple feature maps. It is possible for some feature maps to be a set of multiple feature maps and others to be a single feature map. By way of example, feature maps A 1006 can be multiple feature maps, each using a variation of the CNN architecture of the example model 1000, and feature maps B 1008 can be a single feature map.

Although the example of FIG. 10 shows a CNN as a part of a fully connected network, other architectures are possible, and this example should not be seen as limiting. There can be more or fewer layers in the CNN. The CNN component for the model can be placed in a different order, or the model can contain additional components or models. In some examples, there are no fully connected components, such as in a fully convolutional network. Additional aspects of the CNN, such as pooling, down-sampling, up-sampling, or other aspects known to a person of ordinary skill in the art, can also be employed.

Example Methods

A method 1100 is shown as a set of blocks that specify operations performed but are not necessarily limited to the order or combinations shown for performing the operations by the respective blocks. Further, any of one or more of the operations can be repeated, combined, reorganized, or linked to provide a wide array of additional and/or alternate methods. In portions of the following discussion, reference may be made to the example device 200 of FIG. 2 or to entities or processes as detailed in FIGS. 3-10, reference to which is made for example only. The techniques are not limited to performance by one entity or multiple entities operating on one device.

FIG. 11 depicts the method 1100 for an optical-ultrasound hybrid device 200. The method 1100 can be performed by the optical-ultrasound hybrid device 200 described herein. At 1102, the optical-ultrasound hybrid device 200 receives first optical data based on light incident or reflected from an eye 700 of a subject. For example, the optical-ultrasound hybrid device 200 can employ optical sensors 214 to optically scan the eye 700. The optical-ultrasound hybrid device 200 can have a light source, which can illuminate the eye 700. Additionally or alternately, the optical sensor 214 can take in light incident from the eye 700 or light reflected from the eye 700, which can have emanated from a source other than the device 200.

At 1104, the optical-ultrasound hybrid device 200 receives first ultrasound data based on reflections of ultrasound signals transmitted at the eye 700. For example, an ultrasound scanner 212 can transmit ultrasound signals to the eye 700 as part of an ocular examination. The ultrasound signals can propagate aided by an optical gel or gel-pad, such as the example gel-pad 704 of FIG. 7. The gel-pad 704 can be, as previously described, automatically placed on the eye 700 by the optical-ultrasound hybrid device 200. The blocks 1102 and 1104 can be performed in any order with respect to one another, including being performed at much the same time as one another.

At 1106, the optical-ultrasound hybrid device 200 generates combined ocular data, the combined ocular data comprising a prediction output 1022 by an ML model 902, where the ML model 902, for example, can be configured to use the first optical data and the first ultrasound data as inputs 906. In some examples, the prediction output 1022 can be one or more of an image, a classification, or a probability. For instance, the prediction output 1022 can be an optical-style image similar to what one can expect from a traditional ophthalmoscope. In another example, the ML model 902 can be trained using at least in part a CNN 1000. Other ML training architectures 908 and other prediction outputs can be used; the foregoing examples are meant to be illustrative and not limiting.

At 1108, the optical-ultrasound hybrid device 200 causes the combined ocular data to be displayed on a display device. In an example, the display device can be a combined ocular ultrasound and ophthalmoscope device such as the device 200, which has a display element 218, as shown by way of example in the display 504 of FIG. 5. In another example, the optical-ultrasound hybrid device 200 can connect to a secondary device via a network interface 216 or an auxiliary device interface 220. The secondary device can be, for example, a smartphone, or some other device with a display element 408. The display element 408 of the secondary device can also in aspects be an input, such as a touchscreen. The optical-ultrasound hybrid device 200 can comprise a housing, which can house the secondary device, for example as in the housing 406 in FIG. 4. Other embodiments and combinations can be envisioned by a person of ordinary skill in the art, which are not specifically disclosed in these examples.

FIG. 12 illustrates the example method of FIG. 11 with additional components. At 1202, the optical-ultrasound hybrid device 200 receives second ultrasound data, the second ultrasound data based on reflections of ultrasound signals at a head of the subject. For instance, a second ultrasound scanner 212 can be used, which scans a portion of the head of a patient 108 that is not the eye 700. The portion of the head can, for example, be a brain of the patient 108.

At 1204, the optical-ultrasound hybrid device 200 predicts, based on the first ultrasound data and the second ultrasound data, an injury score related to a level of confidence that a type of injury has occurred. In some examples, the injury score can be a multidimensional object, where each dimension can represent a different type of injury. For example, the injury score can be a two-dimensional pair of numbers, each between 0 and 1. According to some embodiments, the first number can represent a percentage confidence that a patient has suffered a concussion, and the second number can represent a percentage confidence that the patient has glaucoma.

In embodiments, a wearable device 500 can be used for rapid trauma assessment, such as on a football field to determine if the patient 108 (e.g., football player, etc.) has suffered a concussion. For instance, using ultrasound, the wearable device 500 can determine intracranial pressure as the pressure can result, in part, in distortions in the eye 700. For ease of use, the wearable device 500 does not need to display an ultrasound image, but rather a probability of concussion, or a binary classification, which can indicate an absence/presence of a concussion. Additionally or alternately, other injury types can be predicted. For example, the injury score can be other than a number between 0 and 1 representing a percentage, the injury score can be represented by something other than a number, etc.

At 1206, the injury score is compared to a threshold value. Again, using the example where the injury score is a number between 0 and 1, the threshold can also be a number between 0 and 1. In this example, the threshold can be 0.5, or more or less. The threshold can be a multidimensional object, such as a two-dimensional number set. Each dimension of an example multidimensional threshold can correspond to an injury type represented in the same dimension of the injury score. In another instance, the injury score can be multidimensional, but the threshold can be a single, scalar value. Other combinations of dimensionality and representation can also be used.

At 1208, responsive to the injury score meeting or exceeding the threshold value, the wearable device 500 provides the injury score as an injury output. This output can, in some implementations, be in the form of a display of the possible injury type on the display element 504. In some examples, the injury output can be a chart or graph. By way of example using a multidimensional injury score with a corresponding multidimensional threshold value, the display element 504 can show a heat map indicating various levels of deviation of the injury score above or below the threshold values, with different colors representing different amounts of deviation. In other examples, the injury output can simply be a message on the display element 504 indicating that markers for the injury have been detected by the wearable device 500. This may, in aspects, indicate that the injury is present.

The wearable device 500 can, in some examples, determine intraocular pressure measurements via ultrasound. The pressure can be used to detect glaucoma. In an example, the wearable device 500 can determine a response time to a light, which can be used to assess ailments (e.g., glaucoma, dementia, etc.). In an example, the wearable device 500 can be used for early detection of diabetes by determining a presence or absence of swollen optical nerves based on the first or second ultrasound data. In an example, the ML model 902 can predict when a retina will detach. For example, the ML model 902 can include a neural network that generates the prediction, since the ocular ultrasound can see layers behind the retina, unlike a simple ophthalmoscope. This prediction can be added to a patient's annual eye exam.

While the foregoing example of a method 1200 for the optical-ultrasound hybrid device 200, as illustrated in FIG. 12, referred to the wearable device 500, it should be understood that the condition of wearability is not required for a device to perform the method 1200. The method 1200 can readily be employed using any number of embodiments of an optical-ultrasound hybrid device, such as, but not limited to, devices 104, 200, 302, 400, and 620.

FIG. 13 illustrates the example method of FIG. 11 with additional components. At 1302, the optical-ultrasound hybrid device 200 receives second optical data based on additional light incident or reflected from the eye 700. In this way, the optical-ultrasound hybrid device 200 can receive both first and second optical data. Likewise, at 1304, the optical-ultrasound hybrid device 200 receives second ultrasound data based on additional ultrasound signals at the eye 700. In this way, the optical-ultrasound hybrid device 200 can receive both first and second ultrasound data.

At 1306, the optical-ultrasound hybrid device 200 creates a data stream comprising data stream members, the data stream members comprising the first optical data, the second optical data, the first ultrasound data, and the second ultrasound data. According to some examples, the first and second optical data can be adjacent in the data stream and the first and second ultrasound data can be adjacent in the data stream. In other examples, each member of the data stream can be placed in an order it was received. For example, if the first optical data and the second optical data are collected during an optical portion of an examination prior to an ultrasound portion, the first and second optical data can come before the first and second ultrasound data. This order can be reversed or otherwise.

In some examples, optical and ultrasound data can be collected concurrently. For example, the first optical data can be collected at the same time as the first ultrasound data and the second optical data can be collected at the same time as the second ultrasound data. According to this example, the first optical data and the first ultrasound data can be tagged as corresponding with one another, and the second optical data and the second ultrasound data can be tagged as corresponding with one another as well.

At 1308, the optical-ultrasound hybrid device 200 generates a quality score vector of a same dimension as the number of members of the data stream, the quality score vector comprising a quality score for each of the data stream members. For example, there can be a quality score associated with the first optical data. The quality score associated with the first optical data can be, for example, a number between 0 and 1, such as 0.5. According to some examples, similar numbers for the first ultrasound data, the second ultrasound data, and the second optical data can be generated. Consider a four-dimensional vector of quality scores where a first member can correspond with the first optical data, a second member can correspond with the second optical data, a third member can correspond with the first ultrasound data, and a fourth member can correspond with the second ultrasound data. For example, the quality score vector can be represented as (0.5, 0.75, 0.2, 0.15). In this example, the specific quality score for the first optical data can be 0.5, for the second optical data can be 0.75, etc.

At 1310, the optical-ultrasound hybrid device 200, responsive to a respective quality score passing a corresponding threshold, removes the corresponding data stream member from the data stream. Taking the example of the quality score vector being represented as (0.5, 0.75, 0.2, 0.15), suppose the threshold is 0.4 and passing the quality threshold is defined as being under the value of the quality threshold. In this example, the first and second ultrasound data can be removed from the data stream. Additionally or alternately, the threshold value can be a multi-dimensional number. For example, the threshold can be represented as (0.6, 0.1), where the first number is a threshold for optical data and the second value is a threshold for ultrasound data. In this example, only the first optical data is removed from the data stream.

At 1312, the optical-ultrasound hybrid device 200 configures the ML model 902 to use the data stream as an input 802. In one example, the data stream comprises the first optical data, the second optical data, the first ultrasound data, and the second ultrasound data. The quality score vector corresponding to the data stream can be, for example, represented as (0.5, 0.75, 0.2, 0.15), and the threshold can be represented as (0.6, 0.1), where the first number is the threshold for optical data and the second value is the threshold for ultrasound data. In this example, the ML model 902 takes the second optical data, the first ultrasound data, and the second ultrasound data as the inputs 802. Other examples can be readily apparent to a person of ordinary skill in the art. Multiple data streams can be used as multiple inputs to the ML model 902.

Figure 14:
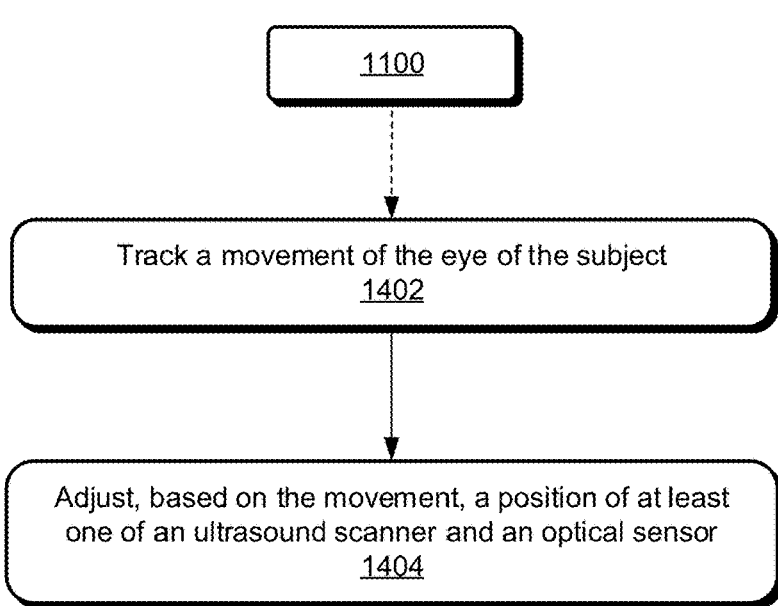
FIG. 14 illustrates the example method of FIG. 11 with additional operations.

FIG. 14 illustrates the example method of FIG. 11 with additional components. At 1402, the optical-ultrasound hybrid device 200 tracks a movement of the eye 700 of the subject (e.g., a patient 108 participating in an ocular examination, etc.). At 1404, the optical-ultrasound hybrid device 200 adjusts, based on the movement, a position of at least one of an ultrasound scanner 212 and an optical sensor 214. According to some implementations, this can allow for an ocular examination of the subject 108 to automatically adjust for the movement of the eye 700, for instance moving the optical sensor 214 to the left responsive to the patient's eye 700 moving in that direction, which can allow the examination to continue without interruption. The movement tracking and subsequent positional adjustment of one or more of the ultrasound scanner 212 and the optical sensor 214 can also, for example, lead to fewer removed images in a data stream such as that discussed regarding FIG. 13.

Various techniques are described in the general context of software, hardware elements, or program modules. Generally, such modules include routines, programs, objects, elements, components, data structures, and so forth that perform particular tasks or implement particular abstract data types. The terms "module," "functionality," and "component" as used herein generally represent software, firmware, hardware, or a combination thereof. In some aspects, the modules described herein (e.g., the training module 908, and the output module 918, etc.) are embodied in a memory 204 of the device 200 as executable instructions or code. Although represented as software implementations, the described modules can be implemented as any form of a control application, software application, signal-processing and control module, hardware, or firmware installed on the device 200.

While a computer-readable storage medium represented as the memory 204 is shown in an illustrative example to be a single medium, the term "computer-readable storage medium" should be taken to include a single medium or multiple media (e.g., a centralized or distributed database and/or associated caches and servers, etc.) that store the one or more sets of instructions. The term "computer-readable storage medium" shall also be taken to include any medium that is capable of storing, encoding, or carrying a set of instructions for execution by the machine and that causes the machine to perform the methods described herein. The term "computer-readable storage medium" shall accordingly be taken to include, but not be limited to, solid-state memories, optical media, and magnetic media.

CONCLUSION

Embodiments of an optical-ultrasound hybrid as described herein are advantageous, as they can enhance a performance of an ocular examination over simply using an ophthalmoscope and/or a separate ocular ultrasound device. Because low power can be required to avoid injury to an eye, a miniaturized and dedicated ocular ultrasound instrument can be implemented. By combining the ocular ultrasound and ophthalmoscope into a single device, a patient can experience a better overall examination. Further, the combination can make combination imagery, which benefits from both optical and ultrasound data, possible for a user to examine. The combined ocular ultrasound and ophthalmoscope can also provide an injury prediction, further resulting in an improvement to the patient's care.

What is claimed is:

1. An optical-ultrasound hybrid device comprising:

a housing;

a first ultrasound scanner coupled to the housing, the first ultrasound scanner configured to generate first ultrasound data, the first ultrasound data based on reflections of ultrasound signals transmitted by the first ultrasound scanner at an eye of a subject;

an optical sensor coupled to the housing, the optical sensor configured to generate optical data, the optical data based on light incident or reflected from the eye;

one or more processors within the housing; and a memory within the housing, the memory storing instructions that, when executed by the one or more processors, cause the one or more processors to:

generate, by a machine-learned (ML) model stored in the memory:

one or more first ultrasound features based on the first ultrasound data; and one or more optical features based on the optical data; and generate, based on the one or more first ultrasound features and the one or more optical features, a hybrid image representing both the first ultrasound data and the optical data.

2. The optical-ultrasound hybrid device of claim 1, further comprising a gel pad distribution mechanism coupled to the housing, the gel pad distribution mechanism configured to place a gel pad on an eyelid of the eye, the gel pad configured to enable propagation of the ultrasound signals between the eyelid and the first ultrasound scanner.

3. The optical-ultrasound hybrid device of claim 1, further comprising one or more second ultrasound scanners coupled to the housing, the one or more second ultrasound scanners configured to generate second ultrasound data, the second ultrasound data based on reflections of second ultrasound signals transmitted by the one or more second ultrasound scanners at a head of the subject, wherein the second ultrasound signals are not transmitted at the eye of the subject.

4. The optical-ultrasound hybrid device of claim 3, wherein the instructions further cause the one or more processors to:

predict, based on at least the first ultrasound data and the second ultrasound data, an injury score comprising a level of confidence that a type of injury has occurred;

compare the injury score to a threshold value; and responsive to the injury score meeting or exceeding the threshold value, provide the injury score as an output.

5. The optical-ultrasound hybrid device of claim 4, wherein the output is at least one of an audio message or a visual message.

6. The optical-ultrasound hybrid device of claim 1, wherein the instructions further cause the one or more processors to:

track a movement of the eye of the subject; and adjust, based on the movement, at least one of an ultrasound position of the first ultrasound scanner or an optical position of the optical sensor.

7. The optical-ultrasound hybrid device of claim 1, wherein the ML model comprises at least in part a convolutional neural network (CNN).

8. The optical-ultrasound hybrid device of claim 1, wherein:

the ML model is a first ML model; and the hybrid image is generated by a second ML model stored in the memory, the second ML model taking at least the one or more first ultrasound features, the first ultrasound data, the one or more optical features, and the optical data as inputs.

9. The optical-ultrasound hybrid device of claim 1, wherein the optical-ultrasound hybrid device is a wearable device.

10. The optical-ultrasound hybrid device of claim 1, wherein the instructions further cause the one or more processors to output the hybrid image to a display device.

11. The optical-ultrasound hybrid device of claim 10, wherein the display device is a smartphone, a tablet computer, or a touchscreen device.

12. The optical-ultrasound hybrid device of claim 10, wherein the display device is stored in the housing.

13. A method for producing an optical-ultrasound hybrid image, the method comprising:

receiving, by a machine-learned (ML) model, first ultrasound data generated by a first ultrasound scanner, the first ultrasound scanner configured to generate the first ultrasound data based on reflections of ultrasound signals transmitted by the first ultrasound scanner at an eye of a subject;

receiving, by the ML model, optical data generated by an optical sensor, the optical sensor configured to generate optical data based on light incident or reflected from the eye;

generating, by the ML model:

one or more first ultrasound features based on first ultrasound data; and one or more optical features based on the optical data; and generating, based on the one or more first ultrasound features and the one or more optical features, a hybrid image representing both the first ultrasound data and the optical data.

14. The method of claim 13, further comprising placing, by a gel pad distribution mechanism, a gel pad on the eye an eyelid of the eye, the gel pad configured to enable propagation of the ultrasound signals between the eyelid and the first ultrasound scanner.

15. The method of claim 13, further comprising generating, by one or more second ultrasound scanners configured to generate second ultrasound data, the second ultrasound data based on reflections of second ultrasound signals transmitted by the one or more second ultrasound scanners at a head of the subject, wherein the second ultrasound signals are not transmitted at the eye of the subject.

16. The method of claim 15, further comprising:

predicting, based on at least the first ultrasound data and the second ultrasound data, an injury score comprising a level of confidence that a type of injury has occurred;

comparing the injury score to a threshold value; and responsive to the injury score meeting or exceeding the threshold value, providing the injury score as an output.

17. The method of claim 13, wherein the ML model comprises at least in part a convolutional neural network (CNN).

18. The method of claim 13, wherein:

the ML model is a first ML model; and the hybrid image is generated by a second ML model, the second ML model using at least the one or more first ultrasound features, the first ultrasound data, the one or more optical features, and the optical data as inputs.

19. The method of claim 13, further comprising outputting the hybrid image to a display device.

20. The method of claim 19, wherein the display device is a smartphone, a tablet computer, or a touchscreen device.

* * * * *